United States Patent
Kim et al.

(10) Patent No.: US 6,534,282 B2
(45) Date of Patent: Mar. 18, 2003

(54) DETECTION OF HYPERTENSION USING IMMUNOREACTIVE METABOLIC PRODUCTS

(76) Inventors: Hyesook Kim, 4683 Ravine Dr., Bloomfield Hills, MI (US) 48301; Jorge H. Capdevila, 6549 Brownlee Dr., Nashville, TN (US) 37205; Raymond R. Novak, 4980 Browning Dr., Orchard Lake, MI (US) 48323; Deanna Kroetz, 373 Dellbrook Ave., San Francisco, CA (US) 94131

(*) Notice: Subject to any disclaimer, the term of this patent is extended or adjusted under 35 U.S.C. 154(b) by 0 days.

(21) Appl. No.: 09/946,644

(22) Filed: Sep. 4, 2001

(65) Prior Publication Data

US 2002/0025544 A1 Feb. 28, 2002

Related U.S. Application Data

(63) Continuation of application No. 09/578,821, filed on May 24, 2000.
(60) Provisional application No. 60/136,475, filed on May 28, 1999.

(51) Int. Cl.$^7$ .................. G01N 33/53; G01N 33/543; G01N 1/00
(52) U.S. Cl. ............... 435/7.92; 435/7.9; 435/174; 435/175; 435/183; 435/4; 435/25; 435/325; 435/348; 435/358; 435/973; 436/174; 436/526; 436/808; 436/811; 436/815; 424/78.1; 424/94.3; 424/182
(58) Field of Search .................. 424/78.1, 94.3, 424/182; 435/325, 348, 358, 4, 7, 7.9, 7.92; 436/518, 526, 808, 815

(56) References Cited

U.S. PATENT DOCUMENTS 5,834,293 A * 11/1998 Capdevila et al. ......... 435/240.1

OTHER PUBLICATIONS

Catella et al. Endogenous biosynthesis of arachidonic epoxides in humans: Increased formation in pregnancy–induced hypertension. Proc. Natl. Acad. Sci. (1990) vol. 87, pp. 5893–5897.*

Nithipatikom et al. Determination of 14,15–Epoxyeicosatrienoic Acid and 14,15–Dihydroxyeicosatrienoic Acid by Fluoroimmunoassay. Anal. Biochem. (1997) vol. 246, pp. 253–259.*

* cited by examiner

*Primary Examiner*—Long V. Le
*Assistant Examiner*—Kartic Padmanabhan
(74) *Attorney, Agent, or Firm*—Kohn & Associates

(57) ABSTRACT

A method to assess hypertension by measuring the amount of free and conjugated hydroxyeicosatrienoic acids (DHETs) and metabolites of DHETs, which are metabolites of arachidonic acid (AA) epoxygenases and epoxide hydrolases, in a biological sample which contains the DHETs (using any methods including GC/MS or ELISA) is disclosed. The method further included determining the amount of molecules containing a DHET-specific epitope immunoreactive with antibodies produced against DHETs present in the sample. This amount is compared with a control sample(s). Hypertension is determined through the comparison wherein the amount of increase of free and conjugated DHETs and metabolites of DHETs in the sample isolated from an organism. The present invention also provides a method to assess catalytic activity of AA epoxygenases using immunoassays by subtracting the amounts of NADPH-independent epoxyeicosatriencic acids (EETs) from total (NADPH-dependent+independent) EETs. The present invention also provides a method to decrease hepatic M epoxygenase expression including 2C23 by treatment of rats with a glucocorticoid including dexamethasone.

9 Claims, 3 Drawing Sheets

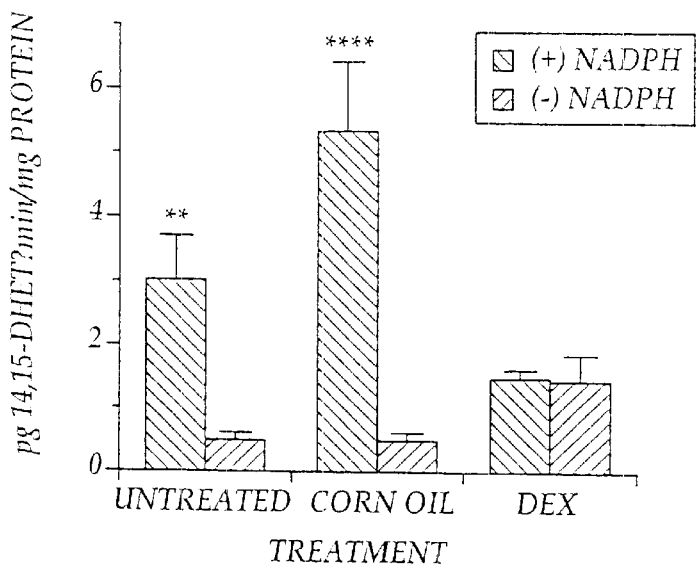
*Figure 3*
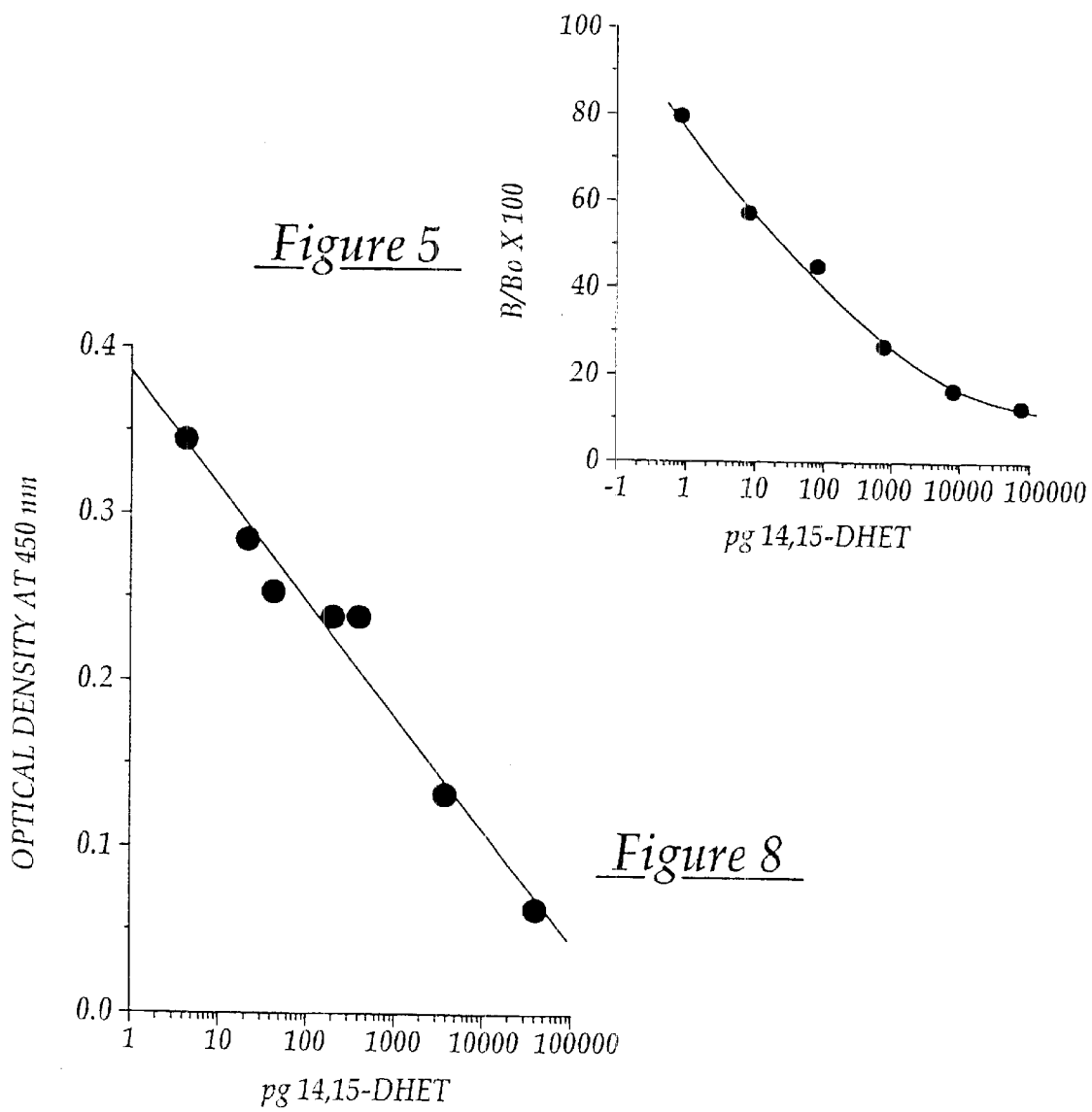
*Figure 5*
*Figure 8*

DETECTION OF HYPERTENSION USING IMMUNOREACTIVE METABOLIC PRODUCTS

CROSS REFERENCE

This is a Continuation application of U.S. Ser. No. 09/578,821 filed May 24, 2000, which is a conversion of U.S. Provisional Application Ser. No. 60/135,475 filed May 28, 1999, both of which are incorporated herein by reference.

GOVERNMENT SUPPORT

Research in this application was supported in part by a contract from National Institute of Environmental Health Sciences (ES 85430). The government has certain rights in the invention.

BACKGROUND OF THE INVENTION

1. Field of the Invention

This invention relates to a method to analyze arachidonic acid (AA)-derived products which are immunoreactive with antibodies produced against hydroxyeicosatrienoic acids (DHETs). More specifically, the present invention relates to a method which can be used to facilitate investigations of the physiological and pathophysiological roles of the metabolic products of arachidonic acid epoxygenases and epoxide hydrolases. The present invention also relates to a method to assess catalytic activity of AA epoxygenases using immunoassays and a method to decrease hepatic AA epoxygenase expression by treatment with glucocorticoids.

2. Description of Related Art

AA is a component of cellular membranes and plays a critical role as a mediator of cell and organ function through its metabolic cascade. The AA cascade includes prostaglandin-synthases, lipoxygenases, and cytochromes P450 (CYPs). The CYP pathway is composed of lipoxygenases-like (allylic oxidation), $\omega/\omega$-1 oxygenases and epoxygenases (olefin epoxidation), which metabolize AA to produce 5-, 8-, 9-, 11-, 12-, and 15-hydroxyeicosatetraenoic acids (HETEs), 16- to 20-hydroxyeicosatetraenoic acids (OH—AAs), and 5,6-, 8,9-, 11,12- and 14,15-epoxyeicosatrienoic acids (EETs), respectively (1). Epoxide hydrolases hydrolyze biologically active EETs to their corresponding dihydroxyeicosatrienoic acids (DHETs).

CYPs which have been identified to be AA epoxygenases are CYP2C11, CYP2C23, CYP2B1, and CYP2B2 expressed in rats (1), CYP2C1 and CYP2C2 expressed in rabbits (2,3), and CYP2C8 and CYP2C9/2C10 expressed in human (4). Recently, CYP2J, a novel CYP subfamily which is abundantly expressed in extrahepatic tissues, has been found in humans (CYP2J2) (5), rats (CYP2J3) (6) and rabbits (CYP2J1) (7).

EETs are synthesized in many tissues including liver, brain, eye, adrenal gland, blood vessels, and kidney, and circulate in blood. EETs are excreted in urine (8–10). Recently, it has been reported that EETs and DHETs are also synthesized in the lung, heart and gastrointestinal tract (5,7,11).

EETs have potent vasoactive properties (vasodilator or vasoconstrictor), increase cytosolic $Ca^+$ concentration and renal $Na^+$ transport, and stimulate hormone release in many tissues including insulin and glucagon from pancreatic islet cells, growth hormone, oxytocin and vasopressin from the pituitary gland, and catecholamines from adrenal gland (9). Recently, it is reported that 14,15-EET functions as a second messenger in epidermal growth factor-mediated signaling pathway (12).

Urinary excretion of $Na^+$, EETs and DHETs decreased after inhibition of AA epoxygenase activity by treating rats with clotrimazole, which induced salt-sensitive and clotrimazoledependent hypertension. A salt-sensitive phenotype of the Dahl rat was associated with a lack of increases in renal AA hypoxygenases after intake of a high salt diet (10,13). A spontaneous hypertensive rat (SHR) study indicated that $\omega/\omega$-1 hydroxylase activity of kidney microsomes was significantly higher than that of normotensive Witstar Kyoto rats (WKY) whereas M epoxygenase activity (EETs+DHETs) showed no difference between two strains at any age group tested (14). Urine samples were not tested. Thus it is generally concluded that the developmental phase of hypertension was linked to increases in the activity of kidney microsomal $\omega/\omega$-1 hydroxylase. Indeed, recently the gene coding for CYP4A2($\omega/\omega$-1 hydroxylase) was found to be preferentially expressed in SHR (14,15).

So far, levels of urinary EETs or DHETs of SHR have not been measured or compared with those of WKY. Thus, our findings that DHET levels in urine specimens obtained from SHR is ~56-fold higher than those of WKY and existence of free and conjugated DHETs and metabolites of DHETs in the SHR urine specimens were surprising. Our result strongly suggest that epoxide hydrolases expressed in kidney play a critical role in hypertension. Thus, measurement of total DHET levels in urine provides better correlation of AA epoxygenase-epoxide hydrolase activities with hypertension.

Levels of EETs in biological specimens, thus far, were measured after chemical hydrolysis to DHETs by high-performance liquid chromatography (HPLC) followed by negative-ion chemical ionization/gas chromatography/mass spectrometry (NICI/GC/MS). This method is not suitable for clinical routines because a) sample preparation for GC/MS is long and tedious, b) The method assesses only free EETs, EETs after chemical hydrolysis to DHIETs, or DHETs and c) it is not practical to measure all the possible EET or DHET metabolites using GC/MS. EET levels in human urine samples and human urine specimens during pregnancy were assayed. However, the EET levels were measured after chemical hydrolysis to DHETs by HPLC/GC/MS (16,17). So, although the data is shown to be DHET, it is only measuring primarily EETs converted to DHET.

Recently free EETs (after chemical hydration to DHETs) were measured by using fluoroimmunoassay (FIA) and radioimmunoassay (RIA) to measure EET release from cells (18). However, again the EET levels of the cell medium extract were measured after chemical hydrolysis of the EETs to DHETs. No prior art reference directs one skilled in the art to the important relationship between the total (free and conjugated) metabolites of AA epoxygenases and epoxide hydrolases and hypertension, nor their measurement in urine samples.

SUMMARY OF THE INVENTION

According to the present invention, a method to assess hypertension mediated by AA epoxygenase and epoxide hydrolase by measuring the amount of DHETs and their metabolites of epoxygenases and epoxide hydrolases in a biological sample which contains[]the DHETs (using any methods including GC/MS or ELISA). The method further included determining the amount of DHET-specific epitopes immunoreactive with antibodies produced against DHETs present in the sample. This amount is compared with a control sample(s). The hypertension mediated by AA epoxygenase and epoxide hydrolase is determined through the comparison wherein the amount of increase in the free and conjugated DHETs and metabolites of DHETs in the sample isolated from an organism. The present invention also provides an immunoassay to assess catalytic activity of AA epoxygenases by subtracting the amounts of NADPH-independent EETs from total (NADPH-dependent +independent) EETs after incubation of the enzyme with NADPH. The present invention also provides a method to decrease hepatic AA epoxygenase expression by treatment with a glucocorticoid including dexamethasone.

DESCRIPTION OF THE DRAWINGS

Other advantages of the present invention will be readily appreciated as the same becomes better understood by reference to the following detailed description when considered in connection with the accompanying drawings wherein:

FIG. 3 is a graph showing assessment of arachidonic acid (AA) apoxygenase activity usina a competitive ELISA against 14,15-dihydroxyeicosatrienoic acid (DHET). AA epoxygenase metabolites, epoxyeicosatrienoic acids (EETs). being chemically hydrolyzed to DHETs prior to the ELISA;

FIG. 5 is a graph showing the sensitivity of IgG produced against 14,15-dihydroxyeicosatrienoic acid (DHET): a typical standard is curve for 14,15-DHET in a competitive ELISA;

FIG. 8 is a graph showing retention of 14,15-dihydroxyeicosatrienoic acid (DHET) in an immunoaffinity column.

DETAILED DESCRIPTION OF THE INVENTION

The present invention generally provides, a method to assess hypertension mediated by AA epoxygenase and epoxide hydrolase by measuring the amount of free and conjugated DHETs and metabolites of DHETs, which are metabolites of AA epoxygenases and epoxide hydrolases. in a biological sample which contains the DHETs. The method further includes determining the amount of molecules containing DHET-specific epitopes immunoreactive with antibodies produced against DHETs present in the sample. This amount is compared with a healthy control sample(s). In general, a panel of healthy control samples is used that are within the normal range. The normal range is established as known in the art and is established for each assay method being utilized, e.g. GC/MS and immunoassays. The hypertension is determined through the comparison wherein the amount of the DHETs is increased in the sample isolated from an organism hypertensive compared to controls.

By assessing hypertension, it is meant that the present inventive assay is capable of being an indication of hypertension. In combination with conventional detection methods, the assay indicates a relationship between hypertension and elevated enzyme activity in the AA cascade. Specifically, the activity of the two enzymes, the epoxygenase and hydrolase which product DHETs, are unexpectedly correlated with the hypertension.

The biological sample can be selected from biological fluids which contain the DHETs and can include, but are not limited to, plasma, urine, cerebrospinal fluids, bile and joint fluids. Urine is the preferred sample.

Figure 1:
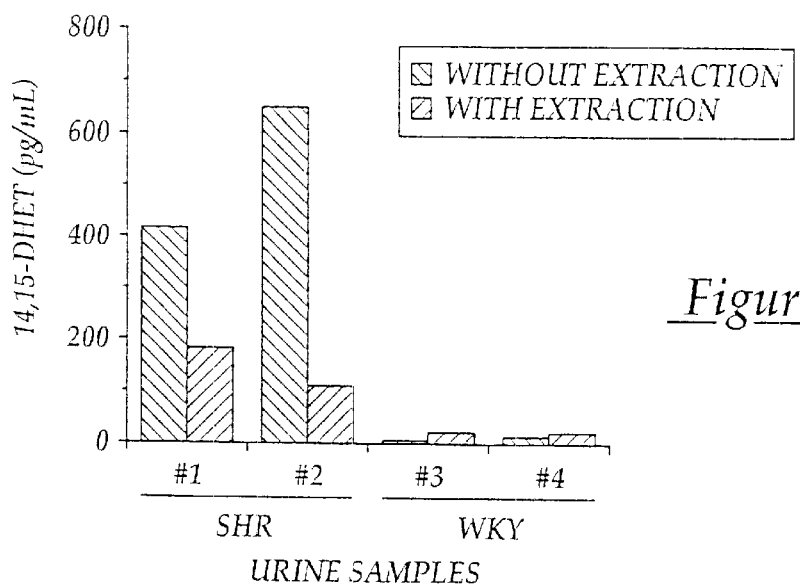
FIG. 1 is a graph showing levels of 14,15-DHET in urine samples obtained from spontaneously hypertensive rats (SHR) and normotensive Wistar Kyoto rats (WKY)

It has been previously shown that AA epoxygenase activities (EETs +DHETs) of kidney cortical microsomes obtained from spontaneously hypertensive rats (SHR) were not different from those of normotensive Wistar Kyoto rats (WKY) (14). Applicants determined DHET levels in urine samples obtained from SHR and compared with those of WKY and found that contrary to the results obtained with kidney cortical microsome study of those rats, urinary DHET levels of SHR were ~56-fold higher than those of WKY (Table 1; FIG. 1). Thus, measurement of urinary DHETs provides better (more specific and more sensitive) assessment of hypertension mediated by AA epoxygenase and epoxide hydrolase (Tables 1 and 2; FIG. 1).

The preferred assay of the present invention, as discussed in detail in the Experiment section herein, is sensitive to both conjugate-free and conjugated forms of DHETs. Recovery rate of $^3$H 14,15- and $^3$H8,9-DHETs spiked in human urine after liquid phase extraction with ethyl acetate was ~100% (Table 3). However, 14,15-DHET levels in urine samples obtained from SHR decreased to the levels lower than ~40% after ethylacetate extraction (Tables 1 and 2; FIG. 1). This result demonstrated that 14,15-DHET exists in the urine as free (ethyl acetate extractable) and conjugated (ethyl acetate unextractable) forms and antibodies produced in accordance with the present invention against 14,15-DHETs recognize both free and conjugated forms. Cross-reactivity of the antibodies with the conjugated form of 14,15- and 8,9-DHETs was further demonstrated by ELISAs using 14,15- and 8,9-DHETs conjugated to bovine serum albumin (FIG. 2, Panels A and B). The antisera recognized the conjugated forms whereas preimmune sera showed only a basal level cross-reactivity with the conjugated forms.

It was surprising that antibodies produced against DHETs a) recognize free (ethyl acetate extractable) and conjugated (ethyl acetate unextractable) forms of DHETs (Tables 1 and 2; FIG. 1);

b) are useful for detection of hypertension related to AA oxygenase and epoxyde hydrolase activities and c) useful for measurement of AA oxygenase (FIG. 3) and epoxide hydrolase activities.

It was unexpected to find that NADPH-independent (AA-epoxygenase-independent) EET formation with hepatic microsomes (FIG. 3). AA-epoxygenase activity analysis using $^{14}$CAA (Table 4) measures only AA-epoxygenase-dependent EET formation whereas assessment of EETs using immunoassays measures both AA epoxygenase-dependent and independent EET formation. Dexamethasone treatment increased AA epoxygenase-independent EET formation activity in liver microsomes (FIG. 3). Subtracting the amounts of NADPH-independent EETs from total (NADPH-dependent+NADPH-independent) EETs after incubation of the enzyme with NADPH provides better assessment of catalytic activity of AA epoxygenases.

Epoxide hydrolase activity also can be measured by the ELISAs against 14,15-DHET because anti-DHET does not recognize 14,15-EET.

Figure 4:
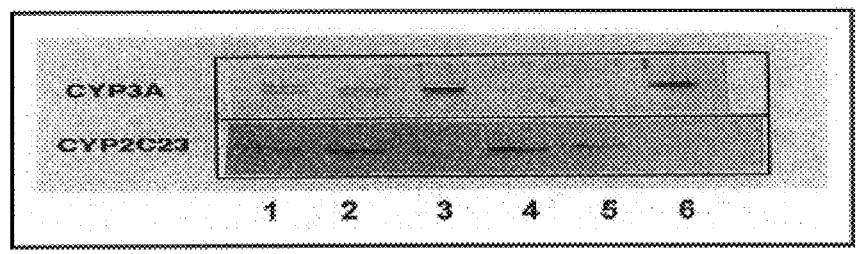
FIG. 4 shows a decrease of hepatic CYP2C23 after treatment of rats with dexamethasone; lanes 1 to 3, hepatic microsomes obtained from male rat; lane 4 to 6, microsomes obtained from female rats; lanes 1 and 4, microsomes obtained from untreated rats; lanes 2 and 5, microsomes obtained from rats after 4 days of corn oil treatment (2 mL/kg/day, i.p.); and lanes 3 and 6, microsomes obtained from rats after 4 days of dexamethasone treatment (10 mg/kg/day, i.p.)

It has been previously shown that CYP2C23 is one of AA epoxygenases expressed in rats. So far, CYP2C11, CYP2C23, CYP2B1, CYP2B2, and CYP2J3 are identified as AA epoxygenases expressed in rats (1). Dexamethasone treatment substantially decreased hepatic AA epoxygenase activity which coincided with decrease in CYP2C23 protein levels (FIG. 4). This unexpected result showed that 2C23 is a predominant AA epoxygenase isoform in the rat liver and hepatic AA epoxygenase expression is lowered by treatment of rats with chemicals such as glucocorticoids including dexamethasone.

In general the quantification of the sample is done utilizing an immunoassay as described in the Examples herein. However alternative immunoassays or GC/MS can be used as the assay in accordance with the present invention. Most of the techniques used in performing immunoassays are widely practiced in the art, and most practitioners are familiar with the standard resource materials which describe specific conditions and procedures. However, for convenience, the following paragraph may serve as a guideline.

In general, ELISAs are the preferred immunoassays employed to assess the amount of EETs and DHETs in a specimen. ELISA assays are well known to those skilled in the ag. Both polyclonal and monoclonal antibodies can be used in the assays. Where appropriate other immunoassays, such as radioimmunoassays (RIAs) or fluoroimmunoassays (FIAs) can be used as are known to those in the art. Available immunoassays are extensively described in the patent and scientific literature. See, for example, U.S. Pat. Nos. 3,791, 932; 3,839,153; 3,850,752; 3,850,578; 3,853,987; 3,867, 517; 3,879,262; 3,901,654; 3,935,074; 3,984,533; 3,996, 345; 4,034,074; 4,098,876; 4,879,219; 5,011,771 and 5,281, 521 and may be adapted to be used the method of the present invention.

The free and conjugated forms of the EETs and DHETs are measured utilizing the immunoassay as set forth for example in the Examples herein with an antibody which recognized both forms. Alternatively, antibodies can be utilized which are specific for each form. Such antibodies can be produced as described herein and tested as set forth in Example 1.

Most of the techniques used to produce antibodies are widely practiced in the art, and most practitioners are familiar with the standard resource materials which describe specific conditions and procedures. However, for convenience, the following paragraphs may serve as a guideline. Antibody production: Antibodies (immunoglobulins) may be either monoclonal or polygonal and are raised against the immunogen. Such immunogens can be used to produce antibodies by standard antibody production technology well known to those skilled in the art as described generally in Harlow and Lane, Antibodies: A laboratory Manual, Cold Spring Harbor Laboratory Cold Spring Harbor, N.Y., 1988 and Borrebaeck, Antibody Engineering-A practical Guide, W. H. Freeman and Co., 1992. Antibody fragments may also be prepared from the antibodies and include Fab, $F(ab')^2$, and Fv by methods known to those skilled in the art.

For producing polycgonal antibodies a host, such as a rabbit or goat, is immunized with the immunogen, generally together with an adjuvant and, if necessary, coupled to a carrier: antibodies to the immunogen are collected from the sera. Further, the polyclonal antibody can be absorbed such that it is monospecific. That is, the sera can be absorbed against related immunogens, e.g. the free and conjugated forms of EETs and DHETs, so that no cross-reactive antibodies remain in the sera thereby rendering it monospecific. Testing for this specificity can be undertaken as described in Example 1.

For producing monoclonal antibodies the technique involves hyperimmunization of an appropriate donor with the immunogen or immunogen fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

For producing recombinant antibody (19) (20) (21), messenger RNAs from antibody producing B-lymphocytes of animals, or hybridoma are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody.

The antibody or antibody fragment can be bound to a solid support substrate or conjugated with a detectable moiety or be both bound and conjugated as is well known in the art to be used in the immunoassay. (For a general discussion of conjugation of fluorescent or enzymatic moieties (22). The binding of antibodies to a solid support substrate is also well known in the art (22) (24). The detectable moieties contemplated with the present invention can include ferritin, alkaline phosphatase, b-galactosidase, peroxidase, urease, fluorescein, rhodamine, tritium, $^{14}C$ and iodination as needed for the immunoassay.

The above discussion provides a factual basis for the method of the present invention to measure total EET and DHET levels including free or conjugated EETs and DHETs, and metabolites of EETs or DHETs as a profile of hypertension of an individual. The methods used with and the utility of the present invention can be shown by the following non-limiting examples and accompanying figures.

EXAMPLES

Materials and Methods

Materials

EETs and DHETs and $^3H$-labeled 14,15- and 8,9-DHETs (higher than 98% pure by HPLC and GC/MS) were provided by Dr. Jorge Capdevila's laboratory. Antibodies against CYP3A and CYP2C23 were obtained from Detroit R&D and Dr. Capdevila's laboratory, respectively.

Horseradish peroxidase-conjugated donkey anti-goat or goat anti-rabbit immunoglobulin G (IgG) and alkaline phosphatase-conjugated donkey anti-rabbit IgG were purchased from Jakson Immuno Research Laboratories, Inc. (West Grove, Pa.). 15(S)HETE, 5(s)15(S)DiHETE, arachidonic acid, Thromboxane $B_2$, $PGE_{2\alpha}$, $PGF_{2\alpha}$, 6-keto-$PGF_{1\alpha}$ were obtained from Biomol Research Lab (Plymouth Meeting, Pa.). Reacti-gel used to cross-link anti-14,15-DHET was purchased from Pierce (Rockford, Ill). Other reagents were obtained from Sigma Chemical Co.

Antibody Production

Synthetic 14, 15- or 8,9-DHETs were coupled to KLH using dicyclohexylcarbodiimide as previously described (25). The conjugate was used to immunize a goat and antibody titers were determined by ELISA using DHET-conjugated bovine serum albumin (BSA).

Purification of IgG Fraction of Antisera

IgG fractions of antibody prepared against 14,15- or 8,9-DHET were purified from sera using protein-G affinity chromatography (Pierce Co.). The IgG bound to the protein G column was eluted with 50 mM glycine-HCl buffer, pH 2.5, and immediately neutralized with 0.5 M tris-HCl, pH 7.6. This procedure did not affect the specificity of the antibodies.

Immunoaffinity Column Chromatography

Reacti-gel was obtained from Pierce Co. and anti-14,15-DHET immunoaffinity column was prepared according to the manufacturer's instruction. Capacity of the immunoaffinity column was measured by applying increasing amounts of 14,15-DHET (FIG. 1). Bound 14,15-DHET was washed with phosphate-buffered saline (PBS), pH 7.4, twice and eluted with acetonitrile:water (1:3), followed by acetone:water (90:10) and quantitated by cLISA. Capacity of the column was ~0.5 µg 14, 15-DHET/100 µl.

Conjugation of 14, 15- or 8,9-DHETs to Horseradish Peroxidase (HRP)

Synthetic 14, 15- or 8,9-DHETs were coupled to HRP using dicyclohexylcarbodiimide as previously described (25).

Solid Phase Competitive Enzyme-Linked Immunaosorbent Assay (ELISA)

High-binding microplates were coated with protein G-purified IgG suspended in 1M carbonate, pH 9.0, (1 µg/well; 200 µl/well final volume) and then covered with paraflim. After overnight incubation at room temperature, the wells were gently washed five times with tris buffered saline (TBS), pH 7.5, containing 0.1% tween. Non-specific sites were blocked by the addition of 0.2 ml of 5% (w/v) nonfat dry milk in TBS. After two hours of incubation at room temperature, they were washed three times with TBS-tween. One µg/well of purified IgG was sufficient for quantitation of 0.5 to 100 pg/well of 14,15- or 8,9-DHETs. Samples and standards (150 µL) were added and the plates incubated for 20 minutes, after which 15 ng of the DHET-HRP conjugate was added in 50 µL of TBS. Following incubation for one hour to permit competitive binding to bound antibody, unbound material was removed by thorough washing of the wells with TBS-tween, and 150 µL of a colorimetric substrate for HRP [3,3',5,5' tetramethylbenzidine (TMB) and hydrogen peroxide] (Sigma Co.) was added. The plate is then incubated for 20 minutes, the reaction stopped by addition of 75 µL of 1N $H_2SO_4$, and the absorbance at 450 nm was determined using a microtiter plate reader. Under these assay conditions, the amount of color in a well is inversely proportional to the initial concentration of the sample or a standard ligand.

Animal Treatment

Male and female Sprague-Dawley (SD) rats (160–200 g) were purchased from Charles River Laboratories (Wilmington, Mass.) and housed in a controlled environment and fed standard laboratory chow for at least 3 days before use. Rats are treated i.p. with dexamethasone (DEX) (10 mg/kg/d, for 4 days) or corn oil (2 ml/kg/d, for 4 days). DEX was dissolved in corn oil.

Rat Urine Collection

Male SHR and WKY rats were purchased from Charles River Laboratories and housed in metabolic cages for up to 3 days and urine was collected over triphenyiphosphine in 24 hour intervals. Aliquots were stored at −80° C.

Preparation of Microsomes

Microsomes were prepared from rat livers and kidneys as described previously (27,28). Microsomes were stored at −80° C. in 50 mM Tris acetate buffer, pH 7.4, containing 1 mM EDTA and 20% glycerol until use.

Protein was assayed by the method of BCA protein assay (Pierce, Rockford, Ill).

Enzyme Assays using $^{14}C$ Arachidonic Acid (AA)

AA epoxygenase activity of microsomes obtained from untreated and rats after treatment with corn oil or DEX was assayed as previously described (1). After incubation of the microsomes (1 mg protein/ml, final concentration), 0.05 M Tris-HCl buffer, pH 7.5, containing 0.15 m KCl, 10 mM $MgC_{12}$, 8 mM sodium isocitrate and 0.5 IU of isocitrate dehydrogenase and, incubated with $^{14}C$ AA (1 µCi/µmol, 100 µM, final concentration) in the presence of 1 mM NADPH at 30° C. The reaction products were taken at five and ten minutes and extracted into ethyl ether containing 0.05% acetic acid. The AA oxygenase metabolites were separated by HPLC and quantitated by a radiomatic Flo-One β-detector.

Enzyme Assays Using ELISA

Microsomes (0.5 mg of protein/ml) in 0.05 M Tris-HCl buffer, pH 7.5, containing 0.15 M KCl, 10 mM $MgCl_2$ and 100 μM AA (total volume, 0.5 ml) were incubated at 35° C. with and without 1 mM NADPH. The EET metabolites were hydrated to DHETs by addition of 20 μl acetic acid and incubated at room temperature for 18 hours. DHETs were extracted with 0.5 ml ethyl acetate and dried under nitrogen. The dried DHETs were reconstituted with TBS and quantitated by ELISA.

Slat Blot Analyses

Slot blot analyses were carried out using alkaline phosphatase system. Visualization was accomplished by incubation with a mixture of 5-bromo4-chloro-3-indolylphosphatate p-toluidine and nitrobluetetrazolium.

Western Blot Analysis

SDS-PAGE was carried out on 10% acrylamide gel. The separated proteins were electroblotted onto cellulose membrane and Western blot analyses were carried out using alkaline phosphatase system as previously described (29). Visualization of P450 bands was accomplished by incubation with a mixture of 5-bromo4-chloro-3-indolylphosphatate p-toluidine and nitrobluetetrazolium.

Statistics

Statistical analysis was carried out using Statview 512 software (Brain Power, Inc., Calabasas, Calif.) and significance between groups was analyzed using one factor anova (Fisher's PLSD).

EXAMPLE 1

DEVELOPMENT OF THE IMMUNOASSAY

Sensitivity Of Antibodies Produced Against 14,15- and 8,9-DHETs

Figure 2A:
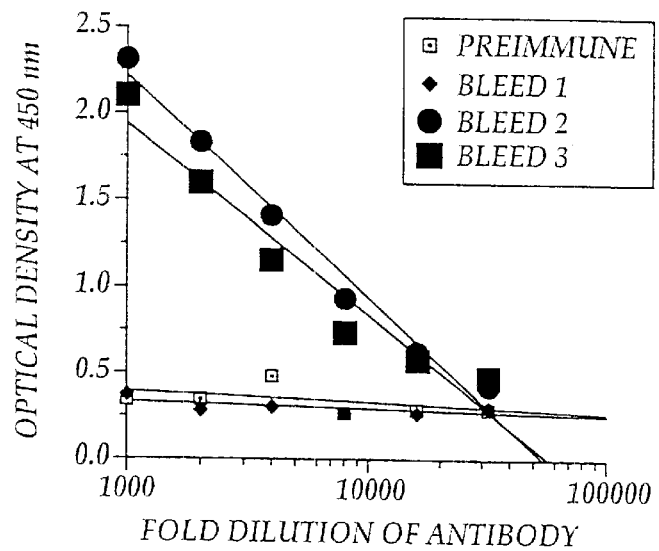
FIGS. 2A–B are graphs showing cross-reactivity of anti-14,15- and 8,9-dihydroxyeicosatrienoic acid (DHET) with DHET conjugated bovine serum albumin (BSA); cross-reactivity of preimmune sera or antibodies produced against 14,15-DHET (Panel A) or 8,9-DHET (Panel B) conjugated to kyehole limpet hemocyanin (KLH) being determined by ELISA; one µg of DHET conjugated BSA per well was coated on plates; whereas preimmune did not show cross-reactivity, immune sera showed strong cross-reactivity with DHET conjugated BSA.
Figure 2B:
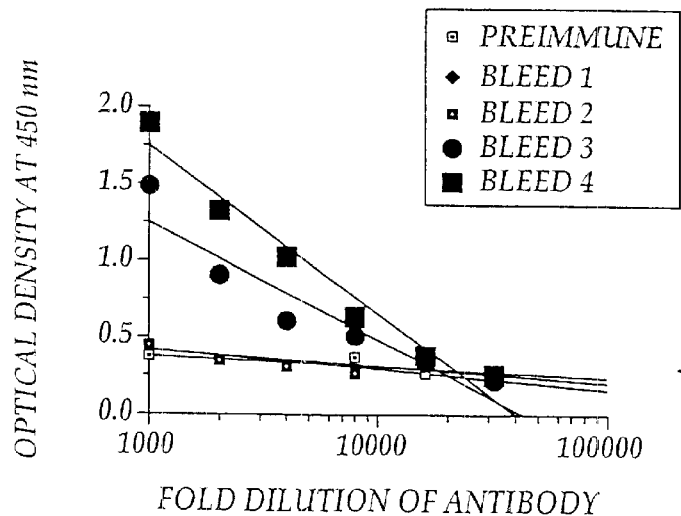

The 2nd and 3rd bleeds of a goat immunized with 14,15-DHET-KLH conjugates showed high binding to 14,15-DHET-BSA conjugates. Whereas preimmune sera of the goat showed binding with 14,15-DHET conjugates at a basal level (FIG. 2A). The 3rd and 4th bleeds of a rabbit immunized with 8,9-DHET-KLH conjugates showed high binding to 8, 9-DHET-BSA conjugates. Whereas preimmune sera of the rabbit showed binding with 8,9-DHET conjugates at a basal level (FIG. 2B).

A typical standard graph for 14,15-DHET is presented in FIG. 5. The $r^2$ value for the fit of the data to an equation describing an inverse logarithmic relationship of free 14,15-DHET to B/Bo was usually higher than 0.96. The detection limits for 14,15- and 8,9-DHET with ELISA were ~1 pg and 10 pg, respectively.

Specificity of Anti-14,15- and 8,9-DHETs

The specificity of the 14,15-DHET ELISA was investigated using authentic DHET and a panel of eicosanoids (Table 5) which, based on their structure, might be anticipated to compete with 14,15-DHET for binding to antibodies against 14,15-DHET. Anti-14,15-DHET did not cross-react with 5,6-, 8,9-, 11,12- or 14,15-EET, 5,6-DHET, 15(S) HETE, 5(s)15(S)DiHETE, arachidonic acid, Thromboxane $B_2$, $PGE_2$, $PGF_{2a}$ or 6-keto-$PGF_{1a}$. There was a slight cross-reaction with 8,9- and 11,12-DHET (3.3% for both).

These result demonstrated that anti-14,15-DHET does not recognize EETs.

Figure 6:
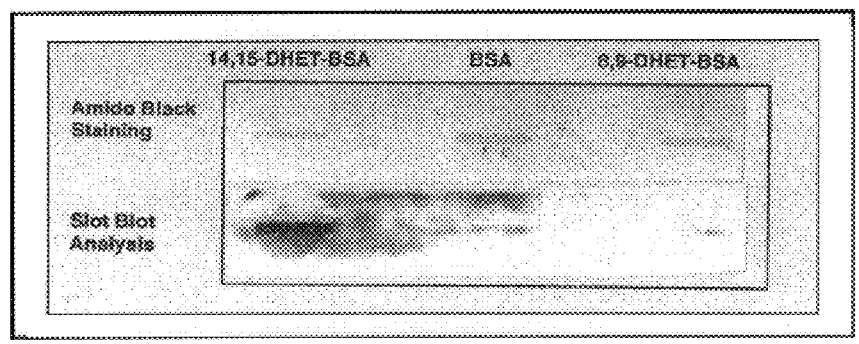
FIG. 6 shows the specificity of anti-14,15-dihydroxyeicosatrienoic acid (DHET) in slot blot analysis.
Figure 7A:
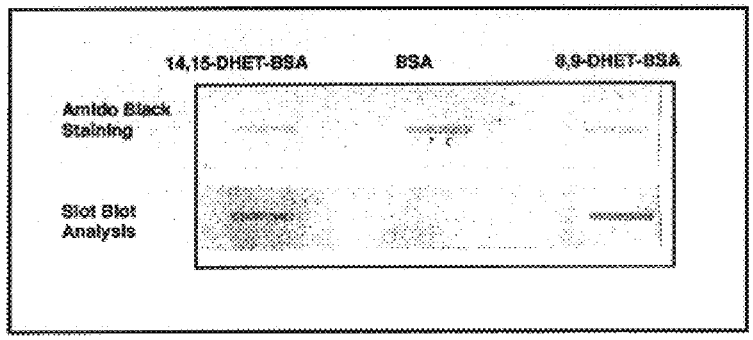
FIGS. 7A–B show the specificity of anti-8,9-dihydroxyeicosatrienoic acid (DHET) is slot blot analyses without (Panel A) and with (Panel B) immunoaffinity column purification.
Figure 7B:
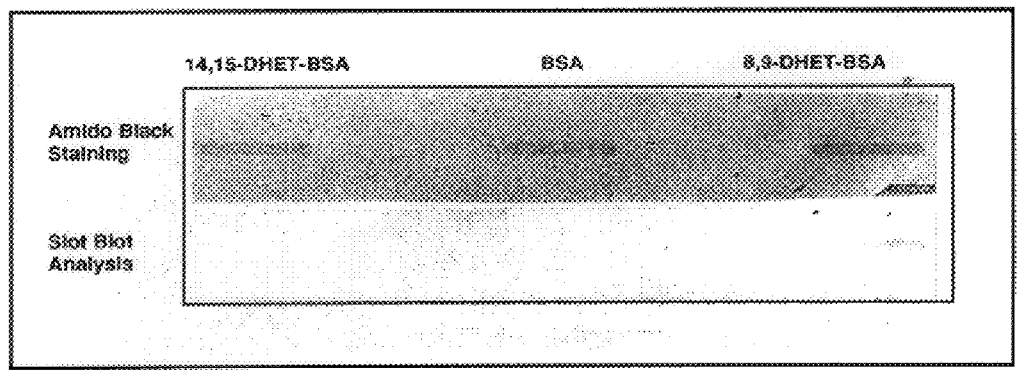

The specificity of the antibody developed against 14,15-DHET was further investigated utilizing slot blot analysis. The 14,15-DHET conjugated BSA, BSA alone and 8,9-DHET conjugated to BSA were blotted onto cellulose membrane. Slot blot analysis was carried out with anti-14, 15-DHET. Though the same amount of protein is loaded to each lane (proteins were visualized by amido-black staining), the antibody cross-reacted with 14,15-DHET conjugated BSA whereas the antibody failed to cross-react with 8,9-DHET which is structurally very similar to 14,15-DHET (FIG. 6). Anti-8,9-DHET cross-reacted with both 8,9- and 14,15-DHETs (FIG. 7, Panel A). Antibodies non-specifically binding to anti-14, 15-DHET were absorbed by incubation of the IgG with anti-14,1 5-DHET immunoaffinity resin. The resultant IgG against 8,9-DHET was form-specific (FIG. 7, Panel B).

The specificity of the anti-14,15-DHET was also investigated utilizing an immunoaffinity chromatography. A 14,15-DHET immunoaffinity coiumn was prepared and increasing amounts of synthetic 14,1 5-DHET were applied to the immunoaffinity column. Levels of 14,15-DHET bound to the column were by ELISA. The bound DHET levels were correlated with levels of 14,15-DHET applied to the column with a correlation coefficient ($r^2$) of 0.97 (FIG. 8). This result demonstrated that, under this experimental condition, the antibody cross-linked to resin bound to 14,15-DHET proportional to the amount of 14,15-DHET applied onto the column.

EXAMPLE 2

Conjugated Forms

Existence of a Conjugated Form of 14, 15-DHET in Urine Specimens $^3$H 14,15-DHET (55,660 cpm) and $^3$H 8,9-DHET (13,899 cpm) were extracted into an equal volume of ethyl acetate. Recovery rates of $^3$H 14,15- and $^3$H 8,9-DHETs after the ethyl acetate extraction were ~100% (Table 3). However, 14.15-DHET levels in urine samples obtained from spontaneously hypertensive rats (SHR) decreased to the levels lower than ~40% after ethyl acetate extraction (Tables 1 and 2; FIG. 1). This result demonstrated that 14,15-DHET exists in the urine as free and conjugated forms and antibodies produced against 14,15-DHETs recognize both free and conjugated forms.

Capability of the 14,15- and 8,9-DHET antibodies to cross-react with conjugated 14,15- and 8,9-DHETs was further demonstrated by immunoassays using 14,15- and 8,9-DHETs conjugated to bovine serum albumin via their carboxyl ends (FIG. 2, Panels A and B).

Free and Conjugated 14,15-DHET Levels in

Urine Specimens of HYeertensive Rats

The levels of 14,15-DHET in urine samples obtained from hypertensive rats (SHR) were measured by ELISA without pretreatment.

The 14,15-DHET levels in hypertensive rats urine specimens were ~56-fold higher than those of normotensive rats (WKY). The values obtained by without pretreatment of urine specimens obtained from SHR were ~2 to 6-fold higher than the levels of these measured by ELISA after ethyl acetate extraction of the urine specimens (Tables 1 and 2; FIG. 1). Levels of 14,15-DHET obtained after purification of urine using ethyl acetate extraction is a measurement of free (or ethyl acetate extractable) 14,15-DHET whereas levels of 14,15-DHET obtained by ELISA without purification of urine is a measurement of both free (ethyl acetate extractable) and conjugated (ethyl acetate unexctractable) DHET. Both free and conjugated forms also contain 14,15-DHET metabolites different from free and conjugated 14,15-DHETs but which retain immunoreactivity with anti-14,15-DHET.

EXAMPLE 3
Measurement of AA Epoxygenase Activity Using ELISA

NADPH-independent (AA epoxygenaseindependent) EET formation with hepatic microsomes was measured (FIG. 3). The AA epoxygenase-independent EET formation activity was higher in hepatic microsomes obtained from rats treated with dexamethasone. Measurement of EET levels using ELISA will measure both AA epoxygenase-dependent and AA epoxygenase-independent EET formation activities. Thus, subtracting the amounts of NADPH-independent EETs from total (NADPH-dependent+NADPH-independent) EETs after incubation of the enzyme with NADPH provides better assessment of catalytic activity of AA epoxygenases. This is contrary to the measurement of AA epoxygenase activity using $^{14}$CAA (Table 4) which measures only AA-epoxygenase-dependent EET formation. Decrease of CYP2C23, a Primary AA Epoxygenase in Liver, by Treatment of Rats Hepatic 3A levels increased after treatment of rats with dexamethasone (FIG. 4). Hepatic CYP2C23 protein level decreased dramatically after dexamethasone treatment of rats (FIG. 4). The decrease of CYP2C23 levels in liver coincided with dramatic decrease of AA epoxygenase activity as measured by ELISA by subtracting the amounts of NADPH-independent EETs from total (NADPH-dependent+NADPH-independent) EETs (FIG. 3) or measurement of AA epoxygenase activity using $^{14}$CAA (Table 4). This result showed that 2C23 is a predominant AA epoxygenase isoform in the rat liver and hepatic AA epoxygenase expression can be lowered by treatment of rats with glucocorticoids including dexamethasone.

Through out this application, various publications, including Unite States patents, are referenced by author and year and patents by number. Full citations for the publications are listed below. The disclosures of these publications and patents in their entireties are hereby incorporated by reference into this application in order to more fully describe the state of the art to which this invention pertains. The invention has been used is intended to be in the nature of words of description rather than of limitation.

Obviously, many modifications and variations of the present invention are possible in the light of the above teachings. It is, therefore, to be understood that within the scope of the appended claims, the invention may be practiced otherwise than as specifically described.

TABLE 1

Levels of 14,15-DHET in urine specimens obtained from spontaneous hypertensive rats (SHR) and normotensive Wistar Kyoto rats (WKY) analyzed by ELISA.

| | 14,15-DHET Levels | | | | |
|---|---|---|---|---|---|
| Sample # | B/Box100/25 µL | pg/25 µL | pg/mL | Mean pg/mL | (Ratio) |
| 1 (SHR) | 58.7 | 10.36 | 414.5 | 532.2 | (56) |
| 2 | 55.4 | 16.25 | 649.9 | | |
| 3 (WKY) | 90.7 | 0.13 | 5.3 | 9.5 | (1) |
| 4 | 83.7 | 0.34 | 13.7 | | |

ELISA was carried out using-horseradish peroxidase system and the bound enzyme conjugate was detected by the addition of 3,3'5,5'-tetra-methylbenzidine (TMB). Reaction was stopped with an acid stop solution and read at 450 nm. Optical density at 450 nm was converted to B/Box100. B, absorbance at 450 nm and Bo, the maximum absorbance reading obtained in the absence of DHET.

TABLE 2

Levels of 14,15-DHET in urine specimens obtained from spontaneous hypertensive rats (SHR) and normotensive Wistar Kyoto rats (WKY) analyzed after ethyl actate extraction by ELISA.

| | 14,15-DHET Levels | | | | |
|---|---|---|---|---|---|
| Sample # | B/Box100/25 µL | pg/25 µL | pg/mL | Mean pg/mL | (Ratio) |
| 1 (SHR) | 58.5 | 4.54 | 181.6 | 145.2 | (7.3) |
| 2 | 61.7 | 2.72 | 108.8 | | |
| 3 (WKY) | 71.9 | 0.53 | 21.2 | 19.8 | (1) |
| 4 | 72.8 | 0.46 | 18.4 | | |

Urine specimen (25 µL) was acidified and extracted with an equal volume of ethyl acetate. The extract was dried under $N_2$ and reconstituted with tris-buffered saline (TBS). ELISA was carried out using horseradish peroxidase system and the bound enzyme conjugate was detected by the addition of 3,3'5,5'-tetra-methylbenzidine (TMB). Reaction was stopped with an acid stop solution and read at 450 nm. Optical density at 450 nm was converted to B/Box100. B, absorbance at 450 nm and Bo, the maximum absorbance reading obtained in the absence of DHET.

TABLE 3

Recovery of $^3$H DHETs spiked in human urine after solid or liquid phase extraction

| | [$^3$H] 14,15-DHET | | [$^3$H] 8,9-DHET | |
|---|---|---|---|---|
| Treatment | CPM | % | CPM | % |
| None | 55,660 | 100 | 13,899 | 100 |
| C18 Solid Phase | | | | |

TABLE 3-continued

Recovery of ³H DHETs spiked in human urine after solid or liquid phase extraction

| Treatment | [³H] 14,15-DHET | | [³H] 8,9-DHET | |
|---|---|---|---|---|
| | CPM | % | CPM | % |
| Extraction | | | | |
| Flow-Through | 1,241 ± 343 | 22.3 ± 0.6 | 260 ± 38 | 1.9 ± 0.3 |
| 1st Elution | 22,544 ± 784 | 40.5 ± 1.4 | 5,294 ± 1,403 | 38.1 ± 10.1 |
| 2nd Elution | 14,247 ± 951 | 25.6 ± 1.7 | 1,928 ± 465 | 13.9 ± 3.3 |
| 3rd Elution | 1,101 ± 73 | 2.0 ± 0.1 | 138 ± 34 | 1.0 ± 0.2 |
| Liquid Phase Extraction with Ethyl Acetate | | | | |
| Extracts | 56,690 ± 850 | 101.9 ± 1.5 | 13,155 ± 334 | 94.6 ± 2.4 |
| Remaining Fractions | 5,342 ± 2,291 | 9.6 ± 4.1 | 852 ± 182 | 6.1 ± 1.3 |

Human urine samples were spiked with ³H 14,15-DHET (55,660 cpm) or ³H 8,9-DHET (13,899 cpm) and acidified to pH 3.0 and extracted into an equal volume of ethyl acetate. Extracts and remaining fractions were counted by a liquid scintillation counter. Alternatively, the spiked urine samples were acidified to pH 3.0 and applied to C-18 solid phase extraction column. The column was first washed with 10% acetonitrile in water, pH 3.0, followed by washing with n-heptane. The bound DHETs were eluted with 1 mL ethyl acetate: heptane (1:1). Elution of DHETs with 1 mL ethyl acetate: heptane (1:1) was repeated until radioactivity of the eluates were low.

TABLE 4

Arachidonic acid (AA) oxygenase activity assays of hepatic microsomes using ¹⁴C AA

| Incubation Time | 14,15-EET | | 11,12-EET | | 8,9-EET + 5,6-EET | |
|---|---|---|---|---|---|---|
| (min) | 5 | 10 | 5 | 10 | 5 | 10 |
| Untreated | 164[a] | 317 | 170 | 493 | 61 | 292 |
| Corn Oil | 231 | 420 | 292 | 585 | 158 | 244 |
| DEX | ND[b] | 97 | ND | 73 | ND | ND |

[a] ng EET formed/mg protein
[b] Not Detectable: Lower than 6.1 ng/mg protein

AA epoxygenase activity of microsomes obtained from untreated and rats after treatment with corn oil or dexamethasone (DEX) was assayed with ¹⁴C AA (1 μCi/μmol, 100 μM, final concentration) in the presence of 1 mM NADPH at 30° C. The reaction products were taken at 5 and 10 min. and extracted into ethyl ether containing 0.05% acetic acid). The AA oxygenase metabolites were separated by HPLC and quantitated by a radiomatic Flo-One B-detector.

TABLE 5

Specificity of anti-14,15-DHET IgG.

| Eicosanoid | % binding of control |
|---|---|
| 14,15-DHET | 100.00 |
| 8,9-DHET | 3.30 |
| 11,12-DHET | 3.30 |

TABLE 5-continued

Specificity of anti-14,15-DHET IgG.

| Eicosanoid | % binding of control |
|---|---|
| 14,15-EET | 1.50 |
| 15(S)HETE | 1.00 |
| 8,9-EET | 0.40 |
| 5(s)15(S)DiHETE | 0.20 |
| 11,12-EET | 0.05 |
| arachidonic acid | 0.05 |
| 5,6-DHET | 0.02 |
| 5,6-EET | 0.02 |
| Thromboxane B2 | 0.02 |
| PGE2 | <0.01 |
| PGF2α | <0.01 |
| 6-keto-PGF1α | <0.01 |

A listing of the panel of eicosanoids used to analyze the specificity of the 14,15-DHET ELISA. These eicosanoids were selected based on the similarity of their structure to 14,15-DHET, as being anticipated to potentially compete with 14,15-DHET for binding to anti-14,15-DHET and thus interfere with such assays.

REFERENCES

1. Capdevila, J. H. Zeldin, D., Makita, K., Karara, A., and Falck, J. R. (1995) in Cytochrome P450: Structure, Mechanism, and Biochemistry (Ed. P. R. Ortiz de Montellano) pp. 443–471, Plenum, New York, N.Y.
2. Laethem, R. M., and Koop, D. R. (1992) Mol. Parmacol. 42, 958–963.
3. Daikh, B. E., Laethem, R. M., and Koop, D. R. (1994) J. Pharmacol. Exp. Ther. 269, 1130–1135.
4. Zeldin, D. C., DuBois, R. N., Falck, J. R., and Capdevila, J. H. (1995) Arch. Biochem. Biophys. 322, 76–86.
5. Wu, S., Moomaw, C. R., Tomer, K. B., Falck, J. R. and Zeldin, D. C. (1996) J. Biol. Chem. 271, 3460–3468.
6. Wu, S., Chen, W., Murphy, E., Gabel, S., Tomer, K. B., Foley, J., Steenbergen, C., Falck, J. R., Moormaw, C. R. and Zeldin, D. C. (1996) J. Biol. Chem. 272, 12551–12559.
7. Kikuta, Y., Sogawa, K., Haniu, M., Kinosaki, M., Kusunose, E., Nojima, Y., Yamamoto, S., Ichihara, K., Kusunose, M. and Fujii Kuriyama, Y. (1991) J. Biol. Chem. 266, 17821–17825.

8. Karara, A., Dishman, E., Blair, I. A., Falck, J. R., and Capdevila, J. H. (1989) J. Biol. Chem. 264,19822–19827.
9. Fitzpatrick, F. A., and Murphy, R. C. (1989) Pharmacol. Rev. 40, 229–241.
10. Makita, K., Falck, J. R., and Capdevila, J. H. (1996) FASEB J. 10, 1456–1463.
11. Zeldin, D. C., Foley, J., Goldsworthy, S. M., Cook, M. E., Boyle, J. E., Ma, Moormaw, C. R., Tomer, K. B., Steenbergen, C. and Wu, S. (1997) Mol. Pharmacol. 51, 931–943.
12. Chen, J.-K., Wang, D.-W., Falck, J. R., Capdevila, J. and Harris, R. C. (1999) J. Biol. Chem. 274, 47644769.
13. Capdevila, J. H., Wei, S., Yan, J., Karara, A., Jacobson, J. R., Falck, J. R., Guengerich, F. P., and DuBois, R. N. (1992) J. Biol. Chem. 267, 21720–21726.
14. Omata, K., Abraham, N. G., Escalante, B. and Schwartzman, M. L. (1992) Am. J. Physiol. 262, F8–F16.
15. Kroetz, D. L., Huse, L. M., Thuresson, A. and Grillo, M. P. (1997) Mol. Pharmacol. 52, 362–372.
16. Toto, R., Siddhanta, A., Manna, S., Pramanik, B., Falck, J. R. and Capdevila, J. (1987) Biochim. Biophys. Acta 919, 132–139.
17. Catella, F., Lawson, J. A., Fitzgerald, D. J. and FitzGerald, G. A. (1990) Proc. Natl. Acad. Sci. USA 87, 5893–5897.
18. Nithipatikom, K., Falck, J. R., and Bhaft, R. K., Hanke, C. J., and Campbell, W. B. (1997) Anal. Biochem. 246, 253–259.
19. Huston et al., 1991 "Protein Engineering of Single-Chain Fv Analogs And Fusion Proteins" in Methods in Enzymology (JJ Langone, ed.; Academic Press, New York, N.Y.) 203:46–88.
20. Johnson and Bird, 1991, "Construction of Single-Chain Fvb Derivatives of Monoclonal Antibodies and Their Production in *Escherichia coli* in Methods in Enzymology (JJ Langone, ed.; Academic Press, New York, N.Y.) 203:88–89.
21. Mernaugh and Menaugh, 1995, "An Ovenriew of Phage-Displayed Recombinant Antibodies" in Molecular Methods in Plant Pathology (RP Singh and US Singh, eds.; CRC Press Inc., Boca Raton, Fla.) pp. 359–365.
22. Johnstone & Thorpe, Immunochemistry in Practice, Blackwell Scientific Publications, Oxford, 1982.
23. Harlow and Lane, Antibodies: A laboratory Manual, Cold Spring Harbor Laboratory, Cold Spring Harbor, N.Y., 1988.
24. Borrebaeck, Antibody Engineering—A practical Guide, W. H. Freeman and Co., 1992.
25. Tijssen, P. (1987) Conjugation of Haptens in Laboratory Techniques in Biochemistry and Molecular Biology (Eds. R. H. Burdon and P. H. van Knippenberg) Vol. 15 Practice and Theory of Enzyme Immunoassays. Pp. 279–296. Elsevier, New York, N.Y.
26. Kaul, K. L. and Novak, R. F. (1987) J. Pharmacol. Exp. Ther. 243, 384–390.
27. Kim, H., Putt, D., Reddy, S., Hollenberg, P. F. and Novak, R. F. (1993) J. Pharmacol. Exp. Ther. 267, 927–936.
28 Kim, H, Kim, S. G., Lee, M. Y. and Novak, R. F. (1992) Biochem. Biophys. Res. Commun. 186, 846–853.

What is claimed is:

1. A method for assessing hypertension in a mammal comprising the steps of only measuring an amount of of free and conjugated dihydroxyeicosatrienoic acids and their metabolites of arachidonic acid converted to dihydroxyeicosatrienoic acid metabolites by both arachidonic acid (AA) epoxygenases and soluble epoxide hydrolases, in a first biological sample; comparing the amount of the free and conjugated dihydroxyeicosatrienoic acids and their metabolites to a second sample from a non-hypertension mammal of a same species and determining if the first mentioned sample contains a comparatively elevated amount of the free and conjugated dihydroxyeicosatrienoic acids and their metabolites as an indication of hypertension mediated by the epoxygenases and epoxide hydrolases.

2. A method as defined in claim 1 wherein said measuring step is further defined as measuring the metabolites in a urine sample.

3. A method as defined in claim 2 further including the steps of obtaining the urine sample; and extracting conjugate-free metabolites from sample before measuring the conjugate-free metabolites.

4. A method as defined in claim 3 wherein said extracting step is further defined as extracting the conjugate-free metabolites in ethylacetate.

5. A method as defined in claim 1 wherein said measuring step is further defined as utilizing GS/MS.

6. A method as defined in claim 1 wherein said measuring step is further defined as utilizing immunoassay.

7. A method as in claim 6 wherein said utilizing step is further defined as applying antibodies produced against 14,15-DHET, which immunologically recognizes both free and conjugated forms of the metabolites, in the immunoassay.

8. A method as defined in claim 7, wherein said measuring step is further defined as determining a specific amount of 14,15 DHET-specific epitopes immunoreactive with antibodies produced against 14,15 DHETs in the first sample and comparing this amount with second sample.

9. A method as defined in claim 1, wherein said comparing step is further defined as comparing an amount of increase in free and conjugated DHETs and metabolites of DHETs in the first sample against the second sample.

* * * * *

UNITED STATES PATENT AND TRADEMARK OFFICE
CERTIFICATE OF CORRECTION

PATENT NO. : 6,534,282 B2 Page 1 of 1
APPLICATION NO. : 09/946644
DATED : March 18, 2003
INVENTOR(S) : Hyesook Kim et al.

It is certified that error appears in the above-identified patent and that said Letters Patent is hereby corrected as shown below:

TITLE PAGE,
(76) Inventors: Hyesook Kim, 4683 Ravine Dr., Bloomfield Hills, MI (US) 48301; Jorge H. Capdevila, 6549 Brownlee Dr., Nashville, TN (US) 37205; Raymond F. Novak, 4980 Browning Dr., Orchard Lake, MI (US) 48323; Deanna Kroetz, 373 Dellbrook Ave., San Francisco, CA (US) 94131

Signed and Sealed this

Third Day of October, 2006

JON W. DUDAS
*Director of the United States Patent and Trademark Office*